United States Patent
Trower et al.

(10) Patent No.: US 10,407,601 B2
(45) Date of Patent: Sep. 10, 2019

(54) MICROABRASIVE COMPOSITIONS CONTAINING OOIDS

(71) Applicant: California Institute of Technology, Pasadena, CA (US)

(72) Inventors: Elizabeth J. Trower, Pasadena, CA (US); Usha F. Lingappa, Pasadena, CA (US); John P. Grotzinger, Pasadena, CA (US); Woodward Fischer, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/905,697

(22) Filed: Feb. 26, 2018

(65) Prior Publication Data

US 2018/0244967 A1 Aug. 30, 2018

Related U.S. Application Data

(60) Provisional application No. 62/463,030, filed on Feb. 24, 2017.

(51) Int. Cl.
| | |
|---|---|
| *C09K 3/14* | (2006.01) |
| *A61K 8/02* | (2006.01) |
| *A61Q 19/00* | (2006.01) |
| *A61K 8/19* | (2006.01) |

(52) U.S. Cl.
CPC ............ *C09K 3/1409* (2013.01); *A61K 8/025* (2013.01); *A61K 8/0241* (2013.01); *A61K 8/19* (2013.01); *A61Q 19/00* (2013.01); *A61K 2800/28* (2013.01); *A61K 2800/412* (2013.01)

(58) Field of Classification Search
CPC .... C09K 3/1409; A61K 8/0241; A61K 8/025; A61K 8/19; A61K 2800/412; A61K 2800/28; A61Q 19/00
See application file for complete search history.

(56) References Cited

U.S. PATENT DOCUMENTS

| | | | |
|---|---|---|---|
| 5,011,512 A | 4/1991 | Wald et al. | |
| 5,102,465 A * | 4/1992 | Lamond | C09C 1/021 |
| | | | 106/464 |
| 5,385,729 A | 1/1995 | Prencipe et al. | |
| 5,531,634 A | 7/1996 | Schott et al. | |
| 5,645,471 A | 7/1997 | Strecker | |
| 5,989,111 A | 11/1999 | Lamphere et al. | |
| 6,080,215 A * | 6/2000 | Stubbs | B24D 3/28 |
| | | | 51/293 |
| 6,511,953 B1 | 1/2003 | Fontana et al. | |
| 10,080,713 B2 * | 9/2018 | Izumikawa | A61Q 1/12 |
| 2001/0004713 A1 | 6/2001 | Lucas et al. | |
| 2010/0015189 A1 * | 1/2010 | Perron | A61K 8/044 |
| | | | 424/401 |
| 2010/0324351 A1 | 12/2010 | Kelemen et al. | |
| 2011/0091955 A1 | 4/2011 | Constantz et al. | |
| 2012/0138103 A1 | 6/2012 | Goyal et al. | |
| 2012/0164042 A1 | 6/2012 | Kelemen et al. | |
| 2012/0225404 A1 | 9/2012 | Kamkar et al. | |
| 2012/0264865 A1 * | 10/2012 | Shaw | C01F 11/185 |
| | | | 524/425 |
| 2012/0291675 A1 | 11/2012 | Camire et al. | |
| 2013/0005015 A1 | 1/2013 | Jovine et al. | |
| 2013/0277046 A1 * | 10/2013 | Haroun | E21B 43/16 |
| | | | 166/248 |
| 2014/0295518 A1 | 10/2014 | Rayalu et al. | |
| 2015/0307401 A1 | 10/2015 | Chen et al. | |
| 2015/0329369 A1 | 11/2015 | Heidel et al. | |
| 2016/0177344 A1 | 6/2016 | Subhas et al. | |
| 2018/0280869 A1 * | 10/2018 | Constantz | B01D 53/62 |

FOREIGN PATENT DOCUMENTS

| | | | |
|---|---|---|---|
| CA | 2971958 A1 | 7/2016 | |
| CN | 102369339 A | 3/2012 | |
| DE | 102007035106 A1 | 2/2009 | |
| EP | 0301885 B1 | 11/1991 | |
| EP | 0291237 B1 | 4/1993 | |
| EP | 502895 B1 | 1/1996 | |
| JP | 59-152306 * | 8/1984 | ............... A61K 7/02 |
| WO | 9803306 A1 | 1/1998 | |
| WO | 2008128331 A1 | 10/2008 | |
| WO | 2018157087 A1 | 8/2018 | |

OTHER PUBLICATIONS

JP59-152306 Machine Translation (Year: 1984).*
International Search Report and Written Opinion for International Application No. PCT/US2018/019777, Search completed Jun. 8, 2018, dated Jun. 8, 2018, 8 Pgs.
"A Science Summary, Environment and Climate Change Canada", Microbeads, Jul. 2015.
"*Browning and Basile* v. *Unilever*, D. Central Cal.", Jul. 24, 2017.
"Microbead ban should include all products washed down the drain, say campaigners", The Guardian, Feb. 8, 2017.
"Plastic Microbeads: Ban the Bead!", Story of Stuff, 2017.
Debaun, "Plastic Microbeads: Tiny Plastics that Pose a Big Problem", Feb. 6, 2014.
Dufault, "Ditching microbeads: the search for sustainable skincare", May 5, 2014.
Eriksen et al., "Microplastic pollution in the surface waters of the Laurentian Great Lakes", Marine pollution bulletin, Dec. 15, 2013, v. 77, No. 1, pp. 177-182.

(Continued)

*Primary Examiner* — Sean M Basquill
(74) *Attorney, Agent, or Firm* — KPPB LLP

(57) ABSTRACT

Ooids, microabrasive compositions containing ooids and methods of making microabrasive compositions containing ooids are described. Generally, ooids represent small particles, which are selectable for size, size distribution, and other characteristics and can be used as a microabrasive particle. Ooids generally show a high level of symmetry, sphericity, roundness and a low aspect ratio. As described here, these characteristics generally yield a predictable and highly effective abrasive.

10 Claims, 8 Drawing Sheets

(56) References Cited

OTHER PUBLICATIONS

Ivar Do Sul et al., "The present and future of microplastic pollution in the marine environment", Environmental Pollution, Feb. 2014, vol. 185, pp. 352-364.
Mason et al., "Microplastic pollution is widely detected in US municipal wastewater treatment plant effluent", Environmental Pollution, Nov. 2016, vol. 218, p. 1045-1054.
Tas, "Aragonite Coating Solutions (ACS) Based on Artificial Seawater", Applied Surface Science, Mar. 1, 2015, vol. 330, pp. 262-269.
Vaughan, "UK government to ban microbeads from cosmetics by end of 2017", Sep. 2, 2016.

* cited by examiner

MICROABRASIVE COMPOSITIONS
CONTAINING OÖIDS

CROSS REFERENCE TO RELATED
APPLICATIONS

This application claims priority to U.S. Provisional Application Ser. No. 62/463,030, entitled "Utility of Ooids and Other Carbonate Sand Grains as Microabrasives" to Trower et al., filed Feb. 24, 2017, which is incorporated herein by reference in its entirety.

FIELD OF THE INVENTION

The present invention is directed to microabrasive compositions, including methods of making thereof. More particularly, the present invention is directed to microabrasives created from ooids with increased homogeneity of size and shape.

BACKGROUND OF THE INVENTION

Plastic microbeads are small synthetic polymer particles, typically smaller than 1 mm in diameter, that were added to a variety of skin care products as gentle abrasive agents; they have also been used in a variety of household and industrial cleaning products. A number of polymers have been commonly added to skin care products, with the most common being polyethylene. (See, e.g., Environment and Climate Change Canada, Microbeads—A Science Summary (July 2015); the disclosure of which is incorporated herein by reference in its entirety.) Within the last several years, there has been growing awareness and concern about these synthetic microbeads as a significant source of microplastic pollution to terrestrial and marine ecosystems (do Sul and Costa, Enviro. Pollution (2014); Eriksen et al., Marine Pollution Bulletin (2013); Mason et al., Enviro. Pollution (2016); the disclosures of which are hereby incorporated by reference in their entirety.) Recent and planned legislation in the United States, Canada, and Europe has sought to curtail and/or ban the use of microbeads in cosmetic products. (MacDonald, Environmental Defence Press Release, (Jun. 29, 2016); H.R. 1321, 114th Cong. (2016); the disclosures of which are hereby incorporated by reference in their entirety.) Even prior to these proposed and planned microbead bans taking effect, some companies have replaced plastic abrasives with alternative particles, including walnut shells, silica gel beads, jojoba wax beads, and other waxes. Walnut shells are the subject of an ongoing lawsuit alleging that the angularity and roughness of this material causes "microtears" in skin. (*Browning v. Unilever US, Inc.*, No. 8:2016cv02210 (C.D. Calif. Filed Dec. 16, 2016); the disclosure of which is incorporated herein by reference in its entirety.) The low density and hydrophobicity of waxes can be problematic for even distribution within various cosmetic materials. While there has not been a comparable public demand for the banning of microplastic abrasives in cleaning products, this too may change and some of the non-plastic particles being used in skincare products (e.g., waxes and silica gel) are likely too soft to be useful alternatives to plastic for these applications. There is, therefore, a clear need for a microabrasive material that is small, microscopically smooth, harder and denser than wax or amorphous silica, and environmentally benign.

SUMMARY OF THE INVENTION

In one embodiment, a microabrasive composition comprises a fluid matrix containing a plurality of ooids, where the ooids possess an average size of at least about 100 μm to less than about 650 μm; a size distribution, where at least 75% of the ooids range from about 75 μm to about 800 μm; an average roundness score of at least 0.4; and an average aspect ratio of less than 1.6.

In another embodiment, the ooids have an average size of about 115 μm and at least 75% of the ooids range from 90 μm to 140 μm.

In a further embodiment, the ooids have an average size of about 200 μm and at least 75% of the ooids range from 150 μm to 250 μm.

In yet another embodiment, the ooids have an average size of about 325 μm and at least 75% of the ooids range from 240 μm to 450 μm.

In still another embodiment, the ooids have an average size of about 635 μm and at least 75% of the ooids range from 480 μm to 800 μm.

In yet still another embodiment, the ooids have an aspect ratio of less than 1.5 and an average roundness of at least 0.5.

In yet a further embodiment, the ooids have an aspect ratio of less than 1.4 and an average roundness of at least 0.7.

In still yet another embodiment, the ooids have an aspect ratio of less than 1.3 and an average roundness of at least 0.75.

In further still another embodiment, the fluid matrix is a personal hygiene product.

In another embodiment, a method for making a microabrasive composition comprising collecting a plurality of ooids from a source; selecting the plurality of ooids for an average size of at least about 100 μm to less than about 650 μm, a size distribution, where at least 75% of the ooids range from 75 μm to 800 μm, wherein the plurality of ooids after selection possess an average roundness score of at least 0.4, and an average aspect ratio of less than 1.6; and combining the plurality of ooids with a fluid matrix.

In a further embodiment, the selecting step is performed using at least one sieve.

In an additional embodiment, the ooids have an average size of about 115 μm and at least 75% of the ooids range from 90 μm to 140 μm.

In a further embodiment, the ooids have an average size of about 200 μm and at least 75% of the ooids range from 150 μm to 250 μm.

In yet another embodiment, the ooids have an average size of about 325 μm and at least 75% of the ooids range from 240 μm to 450 μm.

In still another embodiment, the ooids have an average size of about 635 μm and at least 75% of the ooids range from 480 μm to 800 μm.

In yet still another embodiment, the ooids have an aspect ratio of less than 1.5 and an average roundness of at least 0.5.

In yet a further embodiment, the ooids have an aspect ratio of less than 1.4 and an average roundness of at least 0.7.

In still yet another embodiment, the ooids have an aspect ratio of less than 1.3 and an average roundness of at least 0.75.

In further still another embodiment, the fluid matrix is a personal hygiene product.

BRIEF DESCRIPTION OF THE DRAWINGS

These and other features and advantages of the present invention will be better understood by reference to the following detailed description when considered in conjunction with the accompanying drawings where.

DETAILED DESCRIPTION

Figure 1:
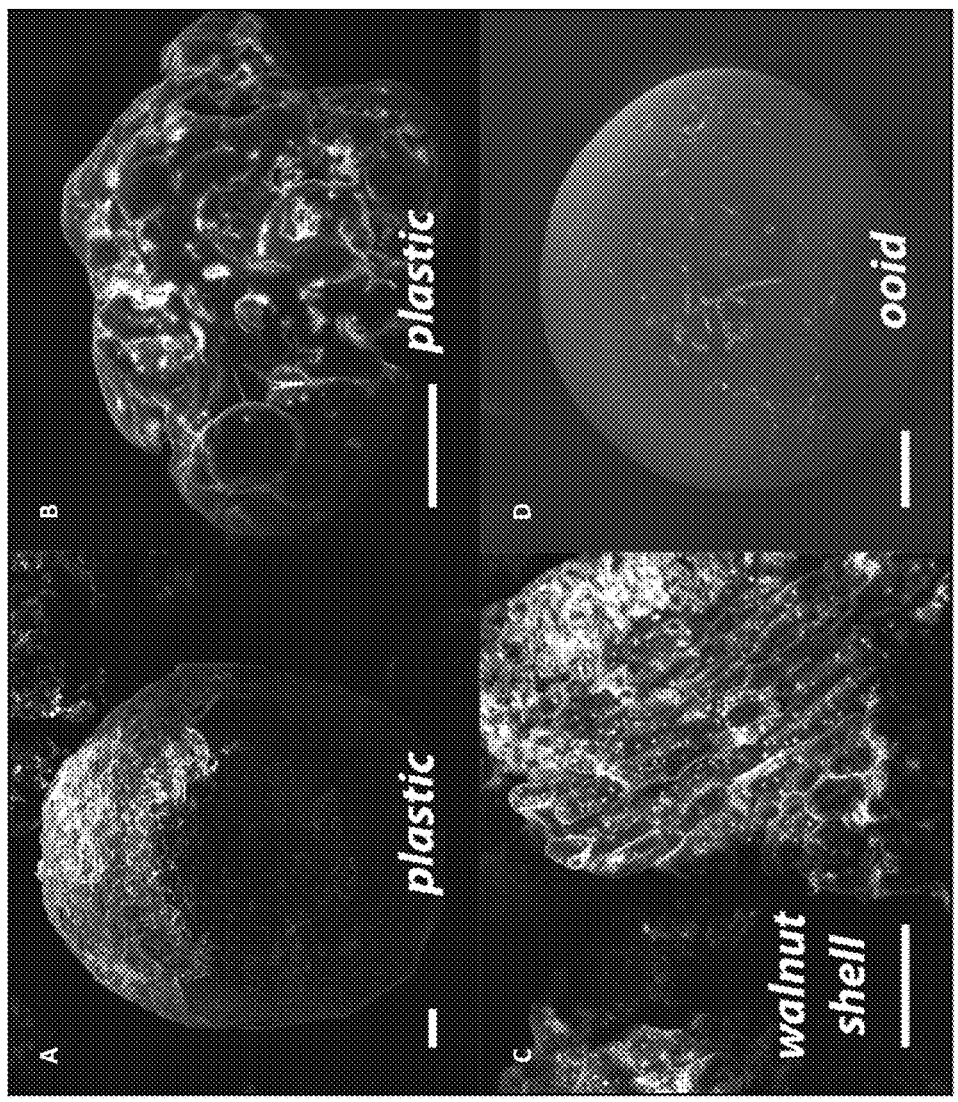
FIG. 1 shows scanning electron microscope images of various microabrasive particles including ooids, in accordance with various embodiments of the invention. In this figure, the scale bar equals 100 μm.

Turning now to the diagrams and figures, embodiments of the invention are generally directed to ooids, microabrasive compositions containing ooids and methods of making microabrasive compositions containing ooids. Generally, ooids represent small particles, which are selectable for size and size distribution. Also ooids generally show a high level of symmetry, sphericity, roundness and a low aspect ratio. These characteristics generally yield a predictable and highly effective abrasive, which can roll and not snag during abrasion, which avoids micro-tears of skin tissue. It should be noted that ooids are also known as oöids. Uses herein of the words ooid, ooids, or oolitic are intended to also reflect and encompass oöid, oöids, and oölitic.

Ooids are a type of well-rounded, well-sorted sand that occur naturally in tropical shallow marine environments and certain lacustrine environments. These sand particles are made of calcium carbonate ($CaCO_3$). Together with other carbonate sand (including abraded and rounded shell fragments), ooids are an ideal natural microbead alternative based on their shape, size, surface texture, chemistry, density, and hardness. Ooids and other carbonate sands can be sourced from tropical marine sands and represent a regenerative resource. After use and during their disposal, all wastewater reactions involving these particles constitute a net carbon sink, opposed to plastic- and wax-based particles.

Non-oolitic carbonate sands are typically composed of shell and other skeletal fragments. These materials also naturally occur in similar sizes to microplastic abrasives, but have more angular shapes and more irregular surface textures if those properties are desirable for a particular application. Both ooids and other carbonate sands are commonly composed of aragonite, though some are composed of calcite or contain mixtures of both $CaCO_3$ polymorphs. The hardness of calcite and aragonite fall in the range of 3-4 on the Mohs hardness scale, somewhat higher halite (NaCl, table salt, 2-2.5 Mohs hardness), which is also used as an abrasive in some skincare products. However, unlike angular cubic halite crystals, carbonate sands, and ooids in particular, tend to be much more rounded and therefore their increased hardness can be offset by their smoother surface textures. The densities of calcite and aragonite, including ooids range from 2.7-2.9 g/cm³, somewhat higher than the density of halite (2.1 g/cm³), but much higher than the density of jojoba wax (0.9 g/cm³) or silica gels (0.7-2.2 g/cm³, depending on porosity), whose lighter-than-water density makes even distribution within a variety of skincare products problematic.

Ooids and other carbonate sand can be sourced from natural environments and are a regenerative resource: ooids are formed as a consequence of shallow marine waters that are supersaturated with respect to $CaCO_3$ and other carbonate sands form via the physical breakdown and abrasion of shell material in high energy beach and shoal environments. At ooid growth rates anticipated from field and empirical constraints and observed in recent experiments, ooid-forming environments seeded with appropriate nuclei have the potential to regenerate sand-sized ooids on the order of under one to several years under optimal current velocities and sediment transport patterns. (Trower et al., Earth and Planetary Science Letters (2017), the disclosure of which is herein incorporated by reference in its entirety.) Preliminary experimental results indicate that ooids are shelf-stable in a variety of commercially available face and body wash products over timescales at least one year. Ooids and other carbonate sands are also natural pH buffers, which would contribute to their long term stability in cosmetic products.

Atmospheric carbon dioxide ($CO_2$)—a known greenhouse gas—absorbs a substantial fraction of outgoing infrared radiation and contributes the predominant increase in radiative forcing—and consequently global temperature change—due to anthropogenic emissions. In contrast with plastic microabrasives, using natural ooids or other carbonate sands as microabrasive materials engenders a net carbon sink of $CO_2$ from the atmosphere. Thus from the perspective of the global carbon cycle, ooids can represent a "green" or at least "greener" consumer alternative to plastic microabrasives.

Carbonate ooids composed of either aragonite or calcite are inert in or can undergo relatively rapid dissolution in solutions under-saturated with respect to these phases primarily due to low relative abundances of calcium ($Ca^{2+}$) and carbonate ($CO_3^{2-}$) ions. As such, ooids require no special remediation. The dissolution in water includes all municipal wastewater and nearly all natural non-marine surface, soil and groundwater. The dissolution process produces two molar equivalents of carbonate alkalinity for every one mole of solid carbonate derived from ooids. The dissolution process constitutes a sink of $CO_2$ from the atmosphere, as shown in Equation 1:

$$CaCO_{3(s)} + H_2O + CO_2 \rightarrow Ca^{2+}_{(aq)} + 2HCO_3^-_{(aq)} \quad (1)$$

Ooids harvested from marine or lacustrine environments constitute a natural source of solid $CaCO_3$ and thus represent a straightforward removal of atmospheric $CO_2$ during their subsequent dissolution post use. The use of ooids combats two sources of pollution and/or environmental impact: reducing the carbon footprint associated with the use of products containing plastic or polymeric microbeads and countering anthropogenic $CO_2$, which is the leading force associated with climate change. With the production of carbonate, ooid use can also act as a pH buffer against corrosion and leaching of unwanted chemicals, including lead, in household or industrial plumbing as well as wastewater systems. Additionally, ooids would not contribute to additional scaling or precipitation in "hardwater" districts. Hardwater districts are water districts in which the water is already saturated with carbonate. The carbonate-saturated water prevents additional addition of carbonate to the water from carbonate-based ooids. Furthermore, any escape of carbonate minerals to the marine system would not pose detrimental environmental effects as they are common sedimentary materials and would act as buffers against ocean acidification.

Although plastic microbeads in cosmetic products have garnered the most popular and media attention recently, their use as microabrasives extends to cleaning products and other materials. A significant problem with plastic microabrasives is that they can pollute the environment. The advantage of ooids and other carbonate sand is as a "greener" alternative to conventional microbeads. However, natural ooids possess a wide-range of sizes, size distributions, and other characteristics (e.g., roundness and sphericity) that may not be beneficial for use as microabrasive particles; thus understanding which specific characteristics make ooids advantageous and selecting ooids for these characteristics provides microabrasive particles that are an advantageous alternative to other microabrasive particles. Additionally the use of ooids is not limited to cosmetic products—ooids can be used for any microabrasive application. The more widely adopted carbonate ooid microabrasives are, the greater their positive impact on the carbon cycle by reducing $CO_2$, a known greenhouse gas, particularly in comparison with microplastics.

Ooid Characterization

Ooids naturally exist in numerous shapes, sizes, size distributions, and other physical characteristics, depending on where they are sourced and how they are formed. For use as a microabrasive particle, certain sizes, shapes, or other characteristics may be more beneficial depending on the specific use. Embodiments of the present invention are directed to ooids selected specific sizes, size distributions, and other physical characteristics discussed below, which make these selected ooids advantageous for use as a microabrasive particle.

Turning now to FIG. 1, typical ooids (Panel D) are 0.25-0.6 mm (250-600 µm) in diameter, well within the range of plastic microbeads harvested from a commercial face wash (Panel A), plastic microbeads harvested from a commercial body wash (Panel B), and crushed walnut shells harvested from a commercial body wash (Panel C). In this figure, the scale bars are equal 100 µm. As seen in Panel D, ooid surfaces are microscopically smooth due to natural polishing by abrasion in the environments in which they occur. This smooth surface differs from the other microabrasive particles, which exhibit coarse surfaces (Panels A and C) or knobby surfaces (Panel B). Additionally, ooids are relatively spherical, well-rounded grains, which is similar to some plastic microbeads (Panels A and B), and ooids are notably and significantly less angular than walnut shell fragments (Panel C). Thus, ooids of some embodiments exhibit different physical characteristics, which may provide an advantage over other microabrasive particles.

Figure 2:
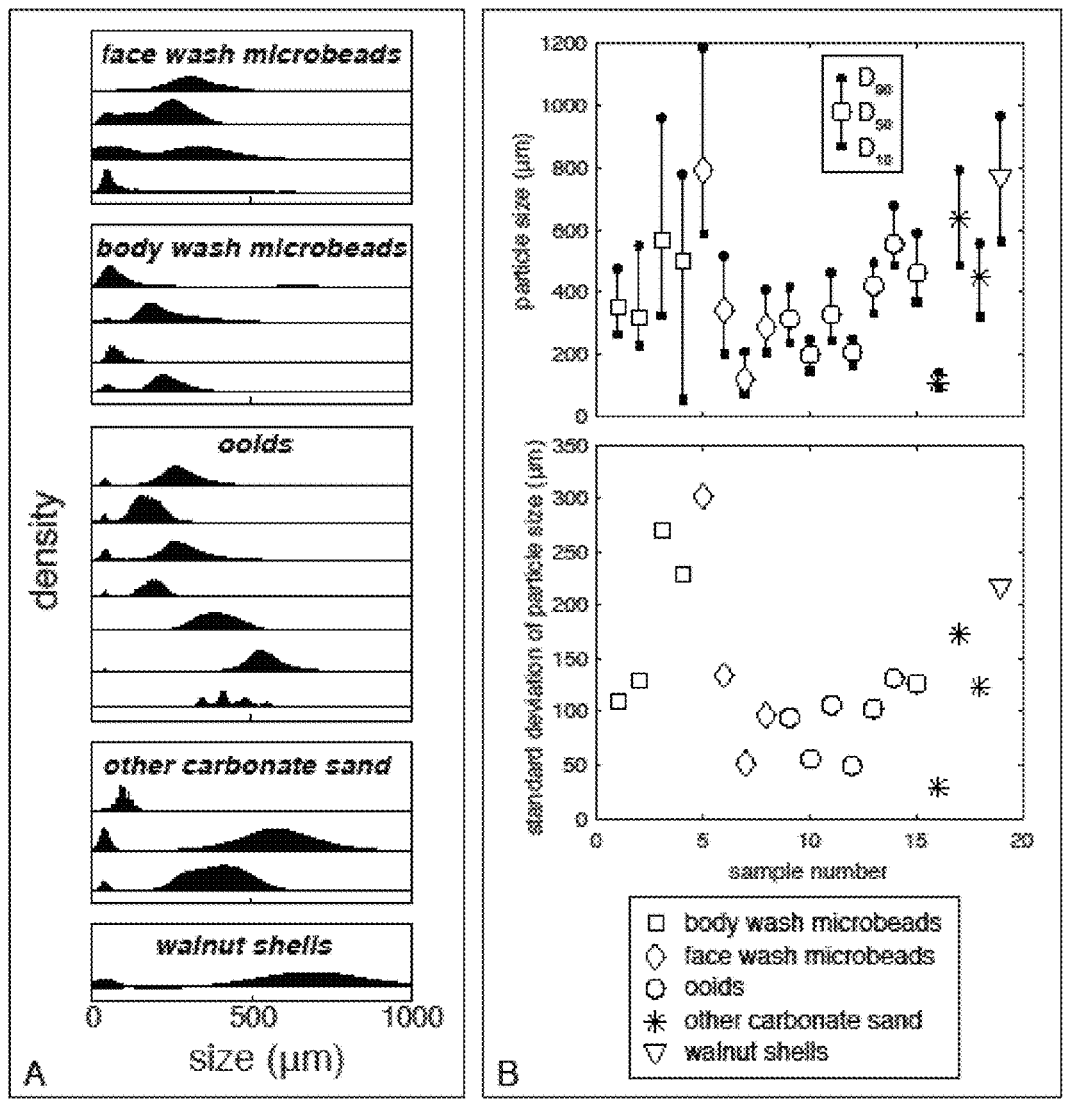
FIG. 2 illustrates the size distribution of various microabrasive particles, including ooids, in accordance with various embodiments of the invention.

Turning to FIG. 2, the data plots illustrate sizes and size distributions of walnut shells, and plastic or polymeric microabrasive particles harvested from various personal hygiene products (e.g., face washes and body washes) in addition to ooids of some embodiments of the invention. As illustrated in FIG. 2, ooids of numerous embodiments demonstrate similar sizes to plastic microbeads and other microabrasive particles. Specifically, Panel A illustrates histograms of the size ranges of samples various types of microabrasive particle, including plastic microbeads harvested from commercial face washes, plastic microbeads harvested from a commercial body washes, ooids in accordance with various embodiments, other forms of carbonate sand, and crushed walnut shells. Panel B graphs size ranges and standard deviation of the various types of microabrasive particles. The upper plot in Panel B illustrates the size distribution as a whisker plot, where the median size, or fiftieth percentile ($D_{50}$), for each sample is plotted as the central point, as represented by a square, diamond, circle, star or triangle for each type of microabrasive particle as denoted in the legend at the bottom of Panel B. The upper whisker ends at the point that represents the ninetieth percentile ($D_{90}$) in the distribution of the microabrasive particles, while the lower whisker ends at the point that represents the tenth percentile ($D_{10}$) in the distribution of the microabrasive particles. The lower graph in Panel B plots the standard deviation of each sample of microabrasive particles.

As shown by the graphs in FIG. 2, ooids of various embodiments may be selected for average sizes ranging from about 100 µm up to about 650 µm. In some embodiments, the average size may be approximately 100 µm, approximately 200 µm, approximately 300 µm, approximately 325 µm, approximately 400 µm, approximately 425 µm, approximately 450, approximately 500 µm, approximately 550 µm, approximately 600 µm, or approximately 650 µm. Further, ooids may be selected for a size distribution where at least 70%, at least 75%, or at least 80% of the ooids exist in a range from about 75 µm to about 800 µm. In some embodiments, the range may be approximately 90 µm to approximately 140 µm, approximately 150 µm to approximately 250 µm, approximately 165 µm to approximately 250 µm, approximately 240 µm to approximately 420 µm, approximately 250 µm to approximately 460 µm, approximately 325 µm to approximately 550 µm, approximately 340 µm to approximately 500 µm, approximately 370 µm to approximately 600 µm, approximately 400 µm to approximately 800 µm, or approximately 490 µm to approximately 700 µm.

As illustrated in FIG. 2, the selection of ooids in various embodiments places these particles within the range of other microabrasive particles rather than a natural distribution of ooid sizes. Additionally, as shown in FIG. 2, ooids of some embodiments may demonstrate a smaller size distribution and lower standard deviation when compared to other microabrasive particles, indicating that the selection of ooids in various embodiments produces microabrasive particles, which are comparable in size to currently used microabrasive products and provide a narrower distribution than would otherwise be available from natural ooids. Further, additional physical characteristics of ooids, such as roundness, aspect ratio, and additional physical characteristics discussed below, may make ooids of certain embodiments an advantageous alternative to other microabrasive particles.

Figure 3:
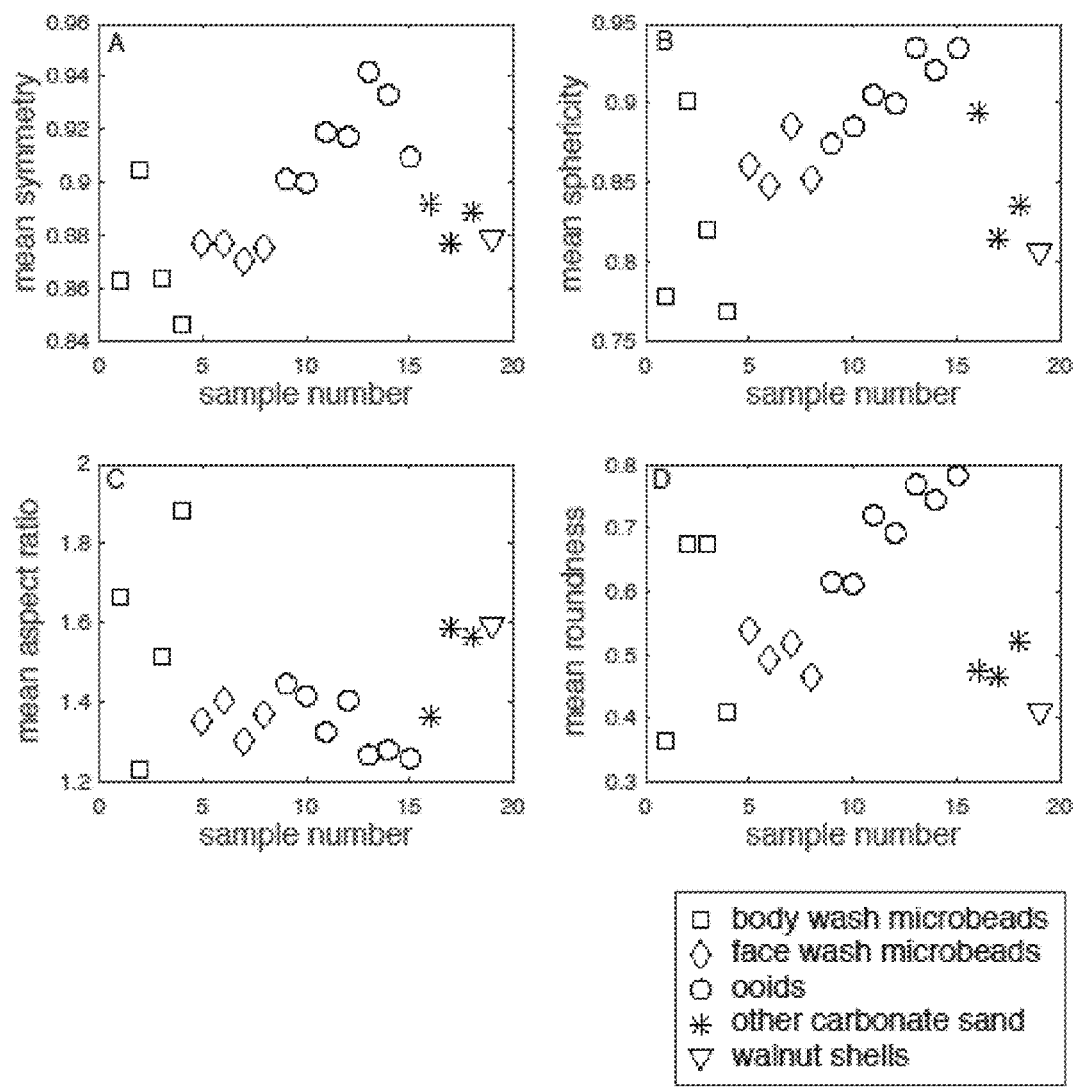
FIG. 3 shows scatter plots describing symmetry, sphericity, aspect ratio, and roundness of various microabrasive particles, including ooids, in accordance with various embodiments of the invention.

Turning now to FIG. 3, various physical characteristics of microabrasives in accordance with embodiments are illustrated. Specifically, FIG. 3 illustrates mean symmetry (Panel A), mean sphericity (Panel B), mean aspect ratio (Panel C), and mean roundness (Panel D). Symmetry is a measure of how much symmetry individual particles exhibit and is scored on a scale of 0 (no symmetry) to 1 (perfect symmetry). Sphericity is a three-dimensional measurement of the divergence of a shape from a perfect sphere. Sphericity is calculated as $4\pi A/P^2$, where P is the perimeter and A is the area of the particle projection. A perfect sphere has a sphericity of unity (scored as a 1 on the scale), while other shapes have a sphericity index of less than 1. Aspect ratio is the ratio of the long axis to the short axis of measurements taken of individual particles from two axes (e.g., length and width). An aspect ratio of 1 means that the two axes are equal, and increasing scores indicates that the two axes are less similar. Roundness is a two-dimensional measurement of the roundness of individual particles using the Wadell Roundness Index. (Wadell, J. of Geology (1932), the disclosure of which is herein incorporated by reference in its entirety). The Wadell Roundness Index is calculated as $\Sigma r_i/(nR)$, where $r_i$ are the radii of curvature of particles' corners, R is the radius of the largest inscribed circle and n is the number of particle corners measured. A score of 1 represents perfectly round particles.

As shown in FIG. 3, ooids of some embodiments may possess greater levels of symmetry (Panel A), sphericity (Panel B), and roundness (Panel C) than other forms of microabrasives. Additionally, ooids of certain embodiments may also possess lower aspect ratios than other forms of microabrasives. Specifically, ooids of various embodiments may possess a higher level of symmetry when compared to other microabrasives, where the symmetry of ooids generally ranges from about 0.87 to about 0.95, such that the mean symmetry of ooids of various embodiments may be at least 0.87, at least 0.88, at least 0.89, at least 0.90, at least 0.91, at least 0.92, at least 0.93, or at least 0.94. Additionally, ooids of some embodiments may possess higher levels of sphericity, when compared to other microabrasives, where sphericity of ooids generally ranges from about 0.80 to about 0.95, such that the mean sphericity of ooids of some embodiments may be at least 0.81, at least 0.83, at least 0.87, at least 0.88, at least 0.89, at least 0.90, at least 0.91, at least 0.92, or at least 0.93. Further, while other microabrasive particles may exhibit aspect ratios of close to 2, ooids of may possess aspect ratios of less than 1.6, such that ooids of numerous embodiments possess aspect ratios of less than 1.6, less than 1.55, less than 1.5, less than 1.45, less than 1.4, less than 1.35, less than 1.3, or less than 1.25. Ooids of many embodiments also may possess higher roundness than other microabrasives, where roundness of ooids generally ranges from about 0.45 to 0.79, such that the roundness of ooids of some embodiments have may be at least 0.45, at least 0.50, at least 0.55, at least 0.60, at least 0.65, at least 0.69, at least 0.70, at least 0.71, at least 0.72, at least 0.73, at least 0.74, at least 0.75, at least 0.76, at least 0.77, or at least 0.78. Thus, ooids selected according to various embodiments show advantageous characteristics in terms of symmetry, sphericity, aspect ratio, and roundness, which do not exist in currently used microabrasive particles and may not exist in naturally occurring ooids.

Figure 4:
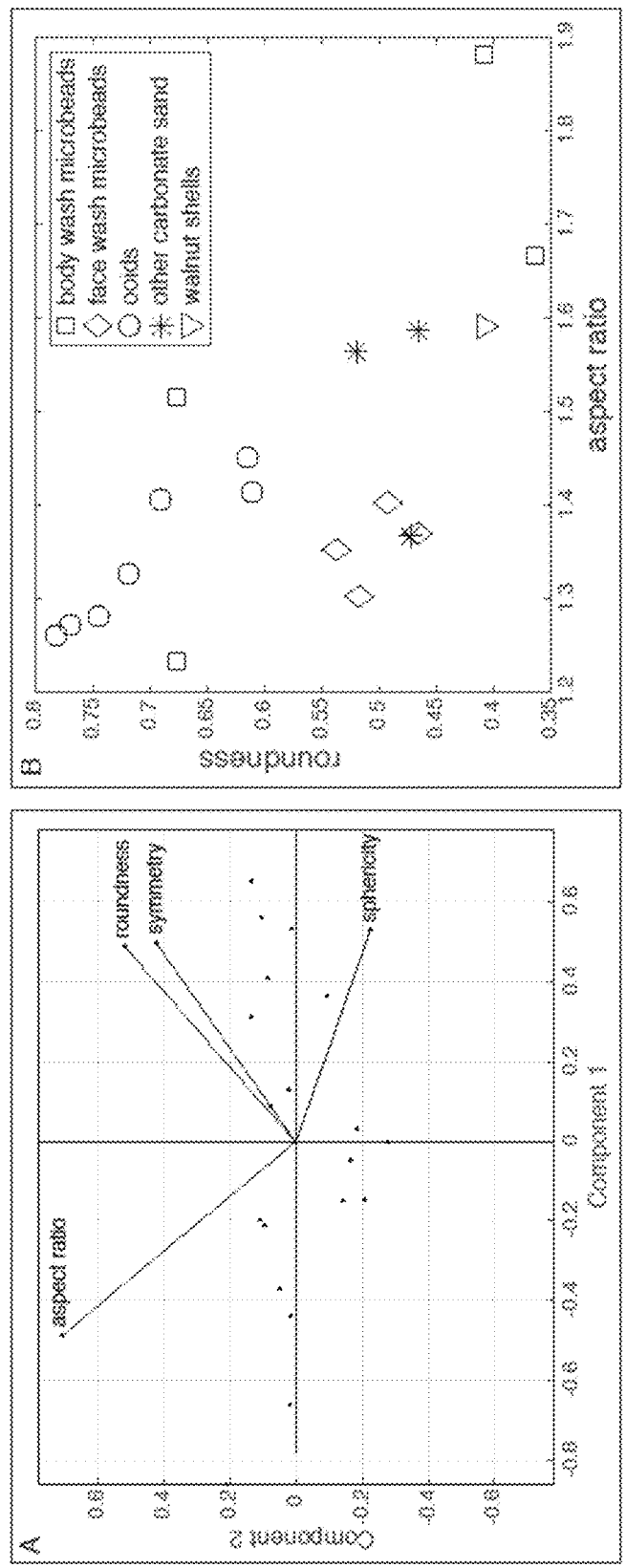
FIG. 4 illustrates a multidimensional analysis of symmetry, sphericity, aspect ratio, and roundness, including a principal components analysis (Panel A) and a scatter plot of aspect ratio versus roundness (Panel B) for various microabrasive particles, including ooids, in accordance with various embodiments of the invention.

Turning now to FIG. 4, a principal components analysis of roundness, aspect ratio, symmetry, and sphericity of various microabrasive particles is plotted in Panel A, while a plot of aspect ratio versus roundness for various microabrasive particles is plotted in Panel B. In Panel A, the principal components analysis shows the vectors for roundness and aspect ratio are nearly perfectly orthogonal, and together, these physical characteristics provide the most useful metrics of microabrasive particle shape. Panel B illustrates the aspect ratio and roundness of various samples of various microabrasive particles. In particular, ooids of various embodiments may form a cluster showing a high level of roundness and low aspect ratio, whereas other carbonate sands and microabrasives harvested from body washes do not form clusters. Additionally, although microabrasives harvested from face washes form a cluster, the cluster does not show a degree of roundness exhibited by ooids of several embodiments. Thus, ooids of certain embodiments may be selected for specific, correlative characteristics, which may not otherwise exist in all ooids from all environments.

Figure 5:
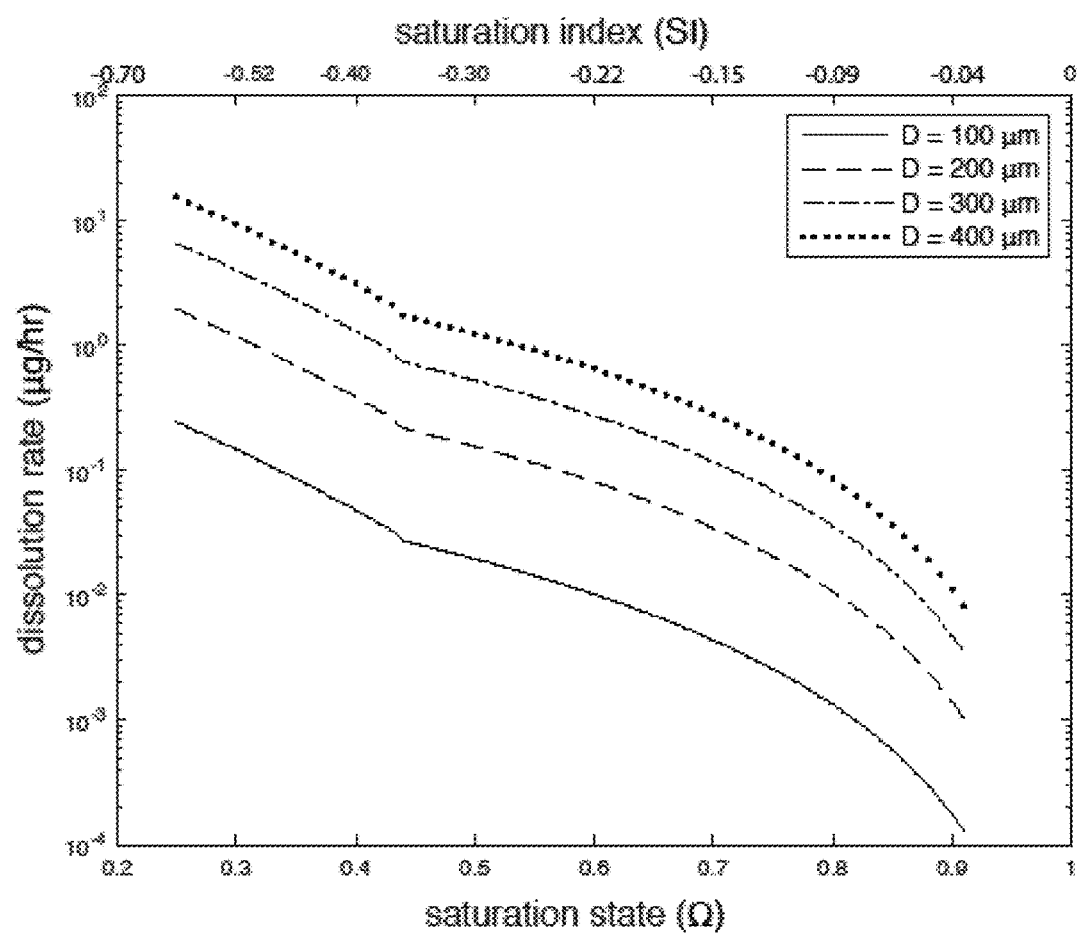
FIG. 5 illustrates the dissolution rate of ooids of various sizes as a function of saturation state, in accordance with various embodiments of the invention.

Turning now to FIG. 5, a graph of the dissolution rates of ooids of certain embodiments is plotted. Carbon dioxide ($CO_2$) in the atmosphere absorbs a substantial fraction of outgoing infrared radiation and contributes the predominant increase in radiative forcing—and consequently global temperature change—due to anthropogenic emissions. In contrast with plastic microabrasives, using either synthetic or natural ooids as microabrasive materials engenders either a net carbon source or net carbon sink, respectively, of $CO_2$ from the atmosphere depending on the processes and mechanisms of their synthesis. Thus from the perspective of the global carbon cycle, ooids can represent a "green" or at least "greener" consumer alternative to plastic microabrasives.

FIG. 5 specifically illustrates the dissolution rate for various sizes of carbonate ($CaCO_3$) ooids as a function of the saturation state ($\Omega$) of household and natural waters. Carbonate ooids composed of either aragonite or calcite undergo relatively rapid dissolution in solutions under-saturated with respect to these phases primarily due to low relative abundances of carbonate ion ($CO_3^{2-}$). This includes all municipal wastewater and nearly all natural non-marine surface, soil and groundwater. The dissolution process produces two molar equivalents of carbonate alkalinity for every one mole of solid carbonate derived from ooids. This process constitutes a sink of $CO_2$ from the atmosphere (Eq. 1).

$$CaCO_{3(s)} + H_2O + CO_2 \rightarrow Ca^{2+}_{(aq)} + 2HCO_3^{-}_{(aq)} \qquad (1)$$

Ooids harvested from marine or lacustrine environments constitute a natural source of solid $CaCO_3$ and thus represent a straightforward removal of atmospheric $CO_2$ during their subsequent dissolution post-use.

The dissolution behavior of grains in natural (drinking, household, gray, and waste) water is described by a Saturation State ($\Omega$)—commonly used measure in geochemistry of the thermodynamic driving force to the equilibrium state. Omega is typically defined as written in Equation 2:

$$\Omega = [Ca^{2+}][CO_3^{2-}]/K_s \qquad (2)$$

where:

$[Ca_2^+]$ and $[CO_3^{2+}]$ denote chemical activities, and $K_s$ reflects the solubility constant.

A related quantity used in hydrology and engineering is the Saturation Index (SI), which is the log of the saturate state ($\Omega$). For drinking water, the SI for calcium carbonate is commonly called the Langelier Saturation Index (LSI). (Langelier, J. of Amer. Water Works Assoc. (1936), the disclosure of which is hereby incorporated by reference in its entirety). The parameter SI is a dimensionless measure of the tendency for the water to dissolve or precipitate carbonate. It is computed as the difference between the measured pH of the water and the pH at calcite saturation ($pH_s$). Negative LSI values dissolve carbonate, while positive LSI values will lead to precipitation of carbonate. The rate of dissolution varies as a function of the deviation from equilibrium. Typical municipal water facilities try to maintain LSI near 0 to avoid strongly corrosive or strongly scaling waters. For well waters the LSI tends to be negative. The USGS has produced large compilations of measurements of LSI from a range of drinking waters sourced. (See Belitz et al., US Geological Survey Scientific Investigations Report 2016-5092 (2016), the disclosure of which is hereby incorporated by reference in its entirety.) According to these exhaustive measurements, the average LSI for well water across the fifty states and the District of Columbia is approximately −0.96. Ooids of some embodiments, which may be present in these waters may help buffer the LSI, and in cases where systems might be corrosive they help raise the LSI via dissolution. Thus, ooids of certain embodiments may be selected based on chemical composition factors that affect dissolution and buffering capacity, which may not be present in ooids comprised of other elements or present in some environments.

Figure 6:
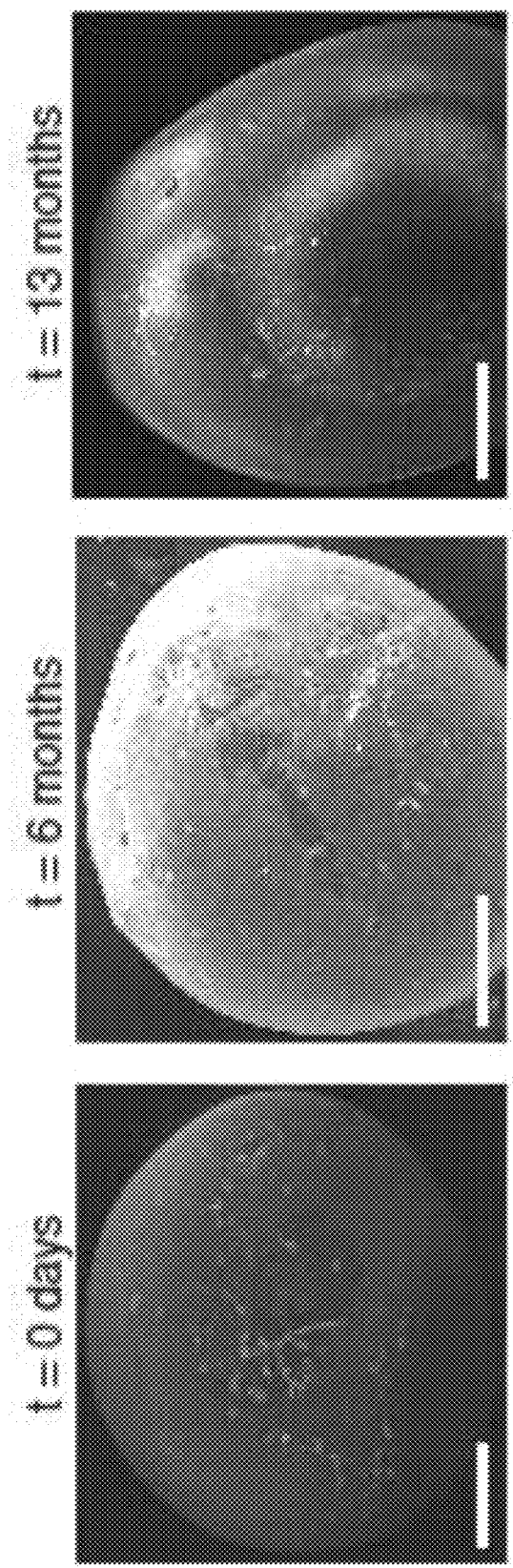
FIG. 6 shows scanning electron microscope images of ooids showing the stability of ooids over time, in accordance with various embodiments of the invention.

Turning now to FIG. 6, scanning electron microscope images demonstrate stability of ooids of various embodiments at 0 months, 6 months, and 13 months (scale bars=100 µm). Ooids of some embodiments may be used in conjunction with a detergent based matrix. Such a matrix could be a personal hygiene product like a face wash, body wash, or any other product that may be used for personal hygiene. Additionally, such a matrix may be an industrial product, which may benefit from the addition of a microabrasive, such as an industrial scrub, polish, liquid sandpaper, or any other industrial product that may benefit from a microabrasive. FIG. 6 demonstrates that ooids of numerous embodiments may remain stable in a commercial body wash for at least one year. The ability to be stable in fluid matrices, which may include detergents, stabilizers, or other components may not be present in all ooids. Thus, ooids of some embodiments may be selected for the ability to remain stable in specific fluid matrices.

Ooids of several embodiments may also be selected for a degree of stickiness. Some microabrasives, such as microabrasives generated from waxes, such as jojoba wax, or plastics and/or polymers may possess characteristics that allow or encourage the microabrasive particles to stick or clump together into larger amalgamations comprising a plurality of individual microabrasive particles. Such clumping or sticking may reduce the efficacy of a composition to work as effectively as a microabrasive, as the number of individual particles will be reduced in the composition. Additionally, clumping or sticking may also reduce the roundness, sphericity, and symmetry in addition to increasing the aspect ratio. These factors may also affect the efficacy of a microabrasive composition, thus sticking and/or clumping may reduce the overall efficacy of a microabrasive composition. Factors that may affect sticking and/or clumping could be heat, humidity, pressure, storage time, stability of the microabrasive particles, certain chemical components in a matrix of a microabrasive composition, and/or any other factor that may lead to individual microabrasive particles sticking and/or clumping together.

Ooids of various embodiments may also be selected for deformability characteristics. Some microabrasive particles may exhibit the ability to deform, or alter shape, under certain circumstances. A desired and/or efficacious shape may be round and/or spherical microabrasive particles, where these microabrasive particles may exhibit the ability to roll across a surface rather than drag. Additionally, microabrasive particles used in personal hygiene products that drag across a surface may cause damage to a person's skin (e.g., walnut shells). Thus, a change of shape away from round and/or spherical may reduce the efficacy of the particles to act in its desired capacity as a microabrasive. Microabrasive particles manufactured from waxes, plastics, polymers and/or other materials may be susceptible to deforming under certain circumstances, such as heat, pressure, time, chemical reactions, and/or any other factor that may have an effect on the material composition of an individual microabrasive particle.

Ooids of certain embodiments may possess smooth surfaces. A smooth surface may be beneficial to certain microabrasive particles, in that a smooth surface may allow a microabrasive particle to slide, glide, and/or roll across a surface. A smooth surface may be desirable in ooids, as the surfaces of some microabrasive particles, such as walnut shells and plastic or polymeric microabrasive particles, may not be smooth. As such, some microabrasive particles, may exhibit dimples, crevices, protrusions, crags, roughness, and/or any other characteristic that differs from smooth. Such external features of a microabrasive particle may cause damage to a surface by dragging, pulling, gouging, scraping, tearing, and/or any other damaging action across a surface. Not all ooids may exist the same level of smoothness, which may provide advantages over a rough or coarse surface. Thus, selecting ooids for surface smoothness may be desirable or beneficial for some uses.

Quality of Ooids as an Abrasive

Figure 7:
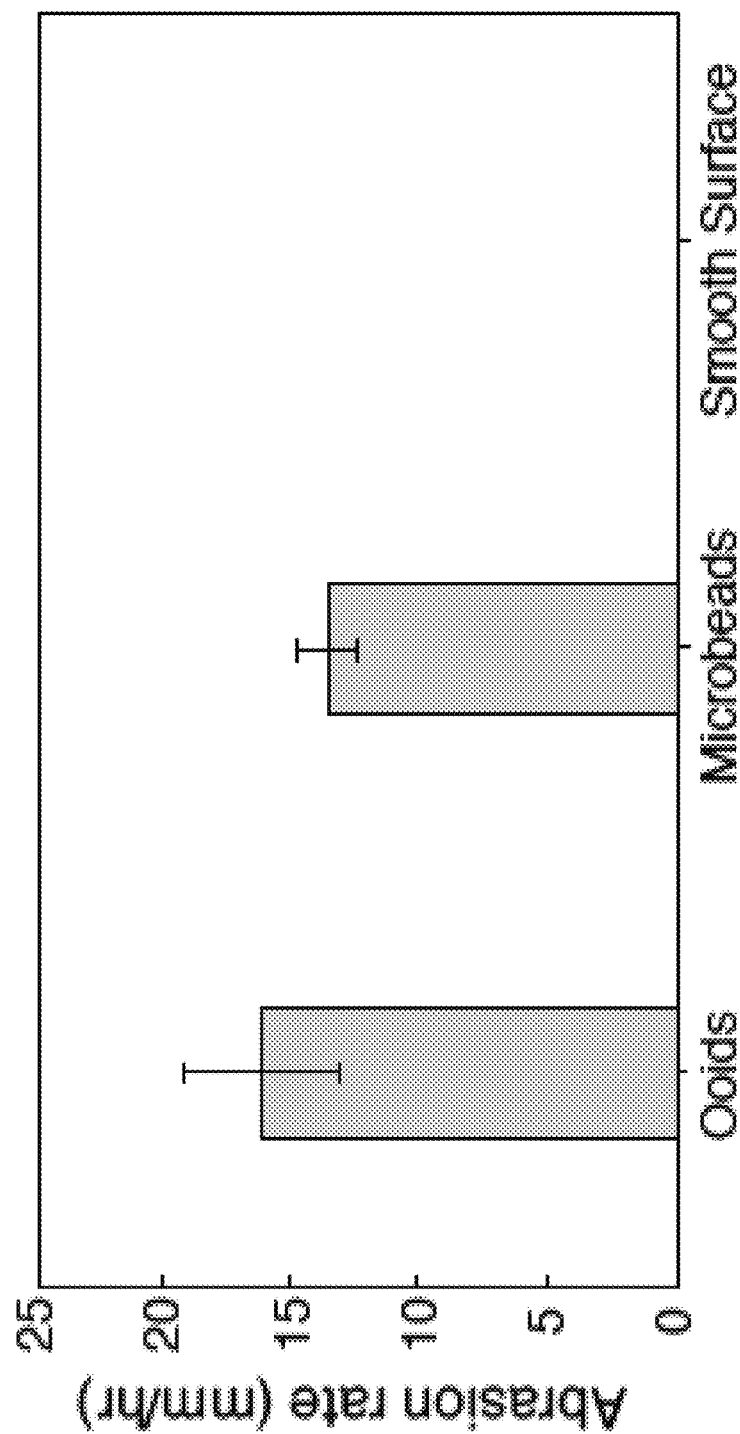
FIG. 7 depicts a bar graph showing the abrasion rates of various microabrasive particles, including ooids, in accordance with various embodiments of the invention.

Turning now to FIG. 7, ooids show similar rates of abrasion as other microabrasive particles. Specifically, FIG. 7 illustrates the abrasion rate (mm/hr) of ooids of various embodiments versus a commercially used microabrasive particle (listed as "Microbeads") and a smooth surface. The assay indicates that ooids of some embodiments exhibit a slightly higher rate of abrasion when compared to commercially used microabrasive particles. The method of performing the assay will be described below.

Uses of Ooids

Some embodiments may be microabrasive compositions containing ooids.

Microabrasive compositions of certain embodiments may contain ooids along with a fluid matrix. The fluid matrix may be gaseous or liquid and may consist of lotions, detergents, pH buffers, nutrients, minerals, stabilizers, and/or any other compound that may be beneficial for a particular use in a microabrasive composition. Microabrasive compositions of various embodiments may be a personal hygiene product, such as face wash, body wash, and/or any other type personal hygiene product. Alternatively, microabrasive compositions of some embodiments may be an industrial product, such as a scrub, polish, liquid sandpaper, or any other industrial product that may include microabrasive particles.

Methods of Making a Microabrasive Composition

Figure 8:
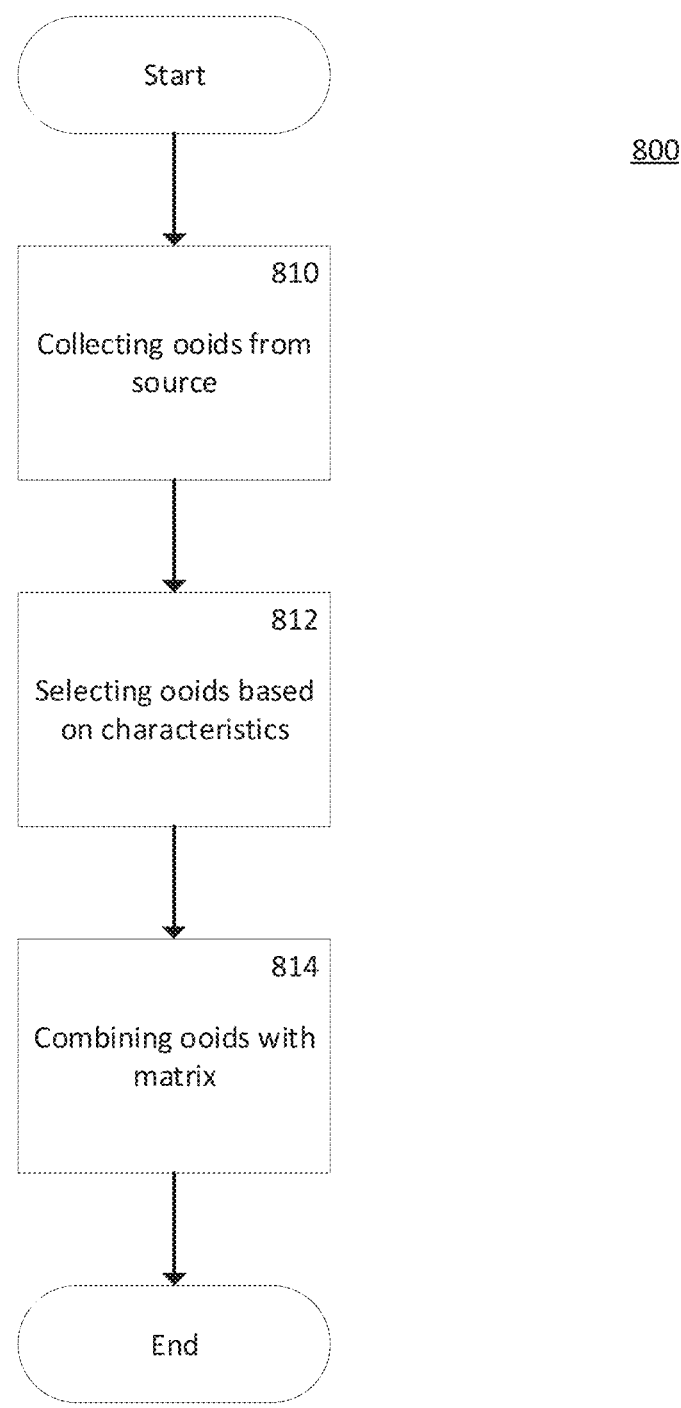
FIG. 8 illustrates a process for making a microabrasive composition, in accordance with various embodiments of the invention.

Turning now to FIG. 8, some embodiments include a method of making a microabrasive composition. This method (800) may include collecting a plurality of ooids from a source (810). As described above, ooids may arise in aquatic environments and show varying characteristics based on the source location. Such sources may include bodies of water, including lakes, oceans, seas, coves, tributaries, gulfs, and/or any other source where ooids are present. Additionally, ooids from a combination of sources may be collected in instances where a variety of sources may be beneficial. However, different sources may produce ooids which do not exhibit the advantageous physical characteristics described herein (e.g., roundness and aspect ratio). Thus, identifying sources which produce ooids with the desired, advantageous characteristics may be beneficial for collecting ooids in accordance with various embodiments.

Collected ooids may further be selected for a variety of characteristics (812), including size, size distribution, roundness, symmetry, sphericity, aspect ratio, degree of smoothness, degree of abrasiveness, degree of dissolution, degree of stability, and/or any other factor that may be beneficial or desired for use of the ooids. Additionally, subsets of collected ooids may be selected for differing characteristics. The selection of the collected ooids may occur by using a filter, sieve, mesh, grating, and/or any other system that allows for the exclusion of certain characteristics. Further, ooids of various embodiments may be selected solely for some features, where the resulting ooids after selection possess additional desirable characteristics. For example, the selection process (812) may select for size and/or size distribution, and the selected ooids possess a desired roundness, aspect ratio, sphericity, and/or symmetry.

The selected ooids may then be combined with a matrix (814). The matrix may be fluid or solid, such that the ooids may be affixed to a solid surface, such as a sandpaper, rasp, plane, and/or any other solid surface used for microabrasion. Additionally, the matrix may be gaseous or liquid. Additionally, a fluid matrix may be of any viscosity or composition for its intended purpose. Further, a fluid matrix may consist of lotions, detergents, pH buffers, nutrients, minerals, stabilizers, and/or any other compound that may be beneficial for a particular purpose in a microabrasive composition. Such purposes may include as a personal hygiene product or an industrial product. Personal hygiene products may be a face wash, body wash, and/or any personal hygiene product, while industrial products may be a scrub, polish, liquid sandpaper, or any other industrial product that may include microabrasive particles.

EXAMPLES

Characterizing Commercially Used Microabrasive Particles

Commercially used microabrasive particles were harvested from commercially purchased personal hygiene products. These products were filtered to collect microabrasive particles. The collected microabrasives were washed with water and allowed to dry.

Microabrasive particles harvested from commercially available products were observed using dynamic image analysis as well as light and scanning electron microscopy. Particle size and shape characteristics, including symmetry, sphericity, aspect ratio, and roundness, were determined using a Retsch Camsizer P4.

Collecting Ooids

Ooids were collected from various locations known for producing ooids, including Turks and Caicos, and Bahama islands and cays, and associated channels and shoals associated with these locations. Ooids were optionally selected for specific sizes using sieves with pores to exclude the passing of various sizes. Collected ooids were then observed using dynamic image analysis as well as light and scanning electron microscopy. Particle size and shape characteristics, including symmetry, sphericity, aspect ratio, and roundness, were determined using a Retsch Camsizer P4.

Measuring Abrasion of Microabrasive Particles

Abrasion experiments were performed by comparing ooids to commercially harvested microabrasive particles; the results of which are illustrated in FIG. 7. Specifically, "microbeads" were harvested from Neutrogena® Face Scrub. Low tensile strength polyurethane foam ($\sigma T=0.32$ MPa) was used as the medium being abraded. Abrasion chambers were constructed by securing a 3.5 cm thick foam disc to the base of a 200 mL beaker, 6.5 cm in diameter. The microabrasive particles being tested were immobilized as a monolayer across a flat surface 4 cm in diameter. The abrasive surfaces were weighted to 80 g, placed in the abrasion chambers, and submerged in water. To insure that any measured abrasion was not merely due to weight, a control was conducted using an identically weighted surface but without any abrasive material (smooth surface). The chambers were sealed with parafilm and shaken at 230 rpm for 1-3 hours. Abrasion was measured as depth scoured in the foam discs by the weighted surfaces. Rates reported here are averages of triplicates, error bars represent standard error between triplicates.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A personal hygiene product formulation comprising:
a fluid matrix containing a plurality of ooids and at least one of the group consisting of a detergent, a lotion, a pH buffer, a nutrient, a mineral, and a stabilizer;
wherein the ooids:
possess an average size of at least about 100 µm to less than about 650 µm;
possess a size distribution, where at least 75% of the ooids range from about 75 µm to about 800 µm;
possess an average roundness score of at least 0.4; and
possess an average aspect ratio of less than 1.6.

2. The personal hygiene product formulation of claim 1, wherein the detergent based matrix is a body wash.

3. The personal hygiene product formulation of claim 1, wherein the detergent based matrix is a face wash.

4. The personal hygiene product formulation of claim 1, wherein the ooids have an average size of about 115 µm and at least 75% of the ooids range from 90 µm to 140 µm.

5. The personal hygiene product formulation of claim 1, wherein the ooids have an average size of about 200 µm and at least 75% of the ooids range from 150 µm to 250 µm.

6. The personal hygiene product formulation of claim 1, wherein the ooids have an average size of about 325 µm and at least 75% of the ooids range from 240 µm to 450 µm.

7. The personal hygiene product formulation of claim 1, wherein the ooids have an average size of about 635 µm and at least 75% of the ooids range from 480 µm to 800 µm.

8. The personal hygiene product formulation of claim 1, wherein the ooids have an aspect ratio of less than 1.5 and an average roundness of at least 0.5.

9. The personal hygiene product formulation of claim 1, wherein the ooids have an aspect ratio of less than 1.4 and an average roundness of at least 0.7.

10. The personal hygiene product formulation of claim 1, wherein the ooids have an aspect ratio of less than 1.3 and an average roundness of at least 0.75.

* * * * *